(12) United States Patent
Xia et al.

(10) Patent No.: US 10,605,761 B2
(45) Date of Patent: Mar. 31, 2020

(54) ELECTROCHEMICAL BIOSENSOR BASED ON APTAMER/NANO SILVER PROBE AND EXO I ENZYME

(71) Applicant: QINGDAO UNIVERSITY, Qingdao, Shandong (CN)

(72) Inventors: Jianfei Xia, Qingdao (CN); Xiyue Cao, Qingdao (CN); Zonghua Wang, Qingdao (CN); Hua Sun, Qingdao (CN)

(73) Assignee: QINGDAO UNIVERSITY, Qingdao (CN)

( * ) Notice: Subject to any disclaimer, the term of this patent is extended or adjusted under 35 U.S.C. 154(b) by 96 days.

(21) Appl. No.: 15/771,251

(22) PCT Filed: Jul. 14, 2017

(86) PCT No.: PCT/CN2017/092880
§ 371 (c)(1),
(2) Date: Apr. 26, 2018

(87) PCT Pub. No.: WO2018/010681
PCT Pub. Date: Jan. 18, 2018

(65) Prior Publication Data
US 2018/0328878 A1  Nov. 15, 2018

(30) Foreign Application Priority Data

Jul. 14, 2016 (CN) .......................... 2016 1 0555404

(51) Int. Cl.
*G01N 27/327* (2006.01)
*G01N 27/333* (2006.01)
(Continued)

(52) U.S. Cl.
CPC ..... *G01N 27/3275* (2013.01); *G01N 27/3276* (2013.01); *G01N 27/3335* (2013.01);
(Continued)

(58) Field of Classification Search
CPC ........... G01N 27/3275; G01N 27/3335; G01N 27/3274; G01N 33/54386; G01N 33/483; C12Q 1/689
See application file for complete search history.

(56) References Cited

FOREIGN PATENT DOCUMENTS

CN  103525815 A  1/2014
CN  104569420 A  4/2015
(Continued)

OTHER PUBLICATIONS

N. M. Danesh, et al. ("A novel electrochemical aptasensor based on arch-shaped structure of aptamer-complimentary strand conjugate and exonuclease I for sensitive detection of streptomycin", Biosensors and Bioelectronics, 75, p. 123-128, (Year: Jan. 2016).*
(Continued)

*Primary Examiner* — J. Christopher Ball
(74) *Attorney, Agent, or Firm* — Oliff PLC (57) ABSTRACT

A electrochemical biosensor based on an aptamer/nano silver probe and an EXO I enzyme. Nano silver nanoparticles having the functions of identifying a target object and generating electrochemical signals and modified by an aptamer are used as a biological probe for detecting target biomolecules, under the initiation of the target object and the assistance of a complementary probe and the EXO I enzyme cyclic shear amplification, and by means of the DNA complementary pairing principle, the probe can be gathered on the surface of a gold electrode, the larger the concentration of the target biomolecules is, the larger the gathering degree of the induced aptamer/nano silver probe is, and meanwhile an EXO I exonuclease target cyclic amplification strategy is introduced in the identification process of the target object, so that the electrochemical biosensor can sensitively and efficiently detect target biological substances.

12 Claims, 1 Drawing Sheet
Specification includes a Sequence Listing.

(51) Int. Cl.
  *G01N 33/543* (2006.01)
  *C12Q 1/689* (2018.01)
  *G01N 33/483* (2006.01)

(52) U.S. Cl.
  CPC ....... *G01N 33/54386* (2013.01); *C12Q 1/689* (2013.01); *G01N 27/3274* (2013.01); *G01N 27/3278* (2013.01); *G01N 33/483* (2013.01)

(56) References Cited

FOREIGN PATENT DOCUMENTS

| CN | 104990966 A | 10/2015 |
|---|---|---|
| CN | 106198673 A | 12/2016 |

OTHER PUBLICATIONS

Sep. 30, 2017 Written Opinion of the International Searching Authority issued in International Patent Application No. PCT/CN2017/092880.

Sep. 30, 2017 International Search Report issued in Patent Application No. PCT/CN2017/092880.

Wang, Li., "Fabrication of Highly Sensitive Electrochemical Nucleic Acid-based Biosensor and Detection Performance.", China Doctoral Thesis Full-text Database (Information Technology).

Danesh, Noor M., et al., "A novel electrochemical aptasensor based on arch-shape structure of aptamer-complimentary strand conjugate and exonuclease I for sensitive detection of streptomycin.", Biosensors and Bioelectronics, vol. 75, pp. 123-128, (2016).

\* cited by examiner

SEQUENCE LISTING

<160> NUMBER OF SEQ ID NOS: 6

<210> SEQ ID NO 1
<211> LENGTH: 16
<212> TYPE: DNA
<213> ORGANISM: Artificial Sequence
<220> FEATURE:
<223> OTHER INFORMATION: capture probe

<400> SEQUENCE: 1
actctttagc cctgat                    16

<210> SEQ ID NO 2
<211> LENGTH: 30
<212> TYPE: DNA
<213> ORGANISM: Artificial Sequence
<220> FEATURE:
<223> OTHER INFORMATION: lysozyme aptamer

<400> SEQUENCE: 2
atcagggcta aagagtgcag agttacttag              30

<210> SEQ ID NO 3
<211> LENGTH: 16
<212> TYPE: DNA
<213> ORGANISM: Artificial Sequence
<220> FEATURE:
<223> OTHER INFORMATION: complementary probe

<400> SEQUENCE: 3
atcagggcta aagagt                    16

<210> SEQ ID NO 4
<211> LENGTH: 17
<212> TYPE: DNA
<213> ORGANISM: Artificial Sequence
<220> FEATURE:
<223> OTHER INFORMATION: capture probe

<400> SEQUENCE: 4
ccaacacaac caacccc                   17

<210> SEQ ID NO 5
<211> LENGTH: 34
<212> TYPE: DNA
<213> ORGANISM: Artificial Sequence
<220> FEATURE:
<223> OTHER INFORMATION: interferon aptamer

<400> SEQUENCE: 5
ggggttggtt gtgttgggtg ttgtgtccaa cccc           34

<210> SEQ ID NO 6
<211> LENGTH: 17
<212> TYPE: DNA
<213> ORGANISM: Artificial Sequence
<220> FEATURE:
<223> OTHER INFORMATION: complementary probe

<400> SEQUENCE: 6
ggggttggtt gtgttgg                   17

ELECTROCHEMICAL BIOSENSOR BASED ON APTAMER/NANO SILVER PROBE AND EXO I ENZYME

FIELD OF THE INVENTION

The present invention relates to the electrochemical detection technology, and in particular to an electrochemical biosensor and its preparation method based on an aptamer/nano silver probe and an EXO I enzyme target cyclic amplification strategy.

BACKGROUND OF THE INVENTION

An electrochemical biosensor is a biosensor which uses bioactive substance (such as enzymes, antibodies, nucleic acids, cells and the like) as bioreceptor) and uses an electrode as a signal converter to convert biochemical signals into electrochemical signals so as to achieve the detection objective. The electrochemical biosensor uses potential, current or capacitance and other electrical signals obtained on the electrode as feature detection signals, has the unique advantages of being simple in instrument, low in manufacturing cost, easy to miniaturize and able to achieve onsite instant detection while having high sensitivity and selectivity, and thus has been widely used in biomedicine, food analysis, environmental monitoring and many other fields.

The traditional electrochemical biosensors can be divided into labeling type biosensors and label-free type of biosensors according to the way of generating the electrochemical signals. The labeling type electrochemical biosensors have been replaced by the label-free type electrochemical biosensors due to complex operation and high cost resulting from that methylene blue, ferrocene and other electroactive substances need to be labeled on DNA chains. The label-free type electrochemical biosensors omit the labeling steps and directly perform the detection by using the electroactive substances in base solutions, such that the cost and the operation complexity can be greatly reduced. However, due to the use of the base solutions, the application range of the label-free type electrochemical biosensors is limited, the back signal is large, the sensitivity is low, and the stability is poor.

Therefore, a label-free type biomolecule detection method with high sensitivity and good stability is needed urgently at present.

SUMMARY OF THE INVENTION

The present invention is based on the deficiencies of the prior art, the objective of the present invention is to provide an electrochemical biosensor based on an aptamer/nano silver probe, and a preparation method and an application thereof. The electrochemical biosensor is used for detecting biomolecules and has the advantages of good selectivity, high sensitivity, etc.

To achieve the above objective, the present invention adopts the following technical solutions:

The first objective of the present invention is to provide a biological probe (referred to as a biological capture probe hereinafter) having the functions of identifying a target object and generating electrochemical signals and being used for detecting target biomolecules, the biological probe includes nano silver and a plurality of probe bodies connected to the surface of the nano silver, each probe body includes an aptamer fragment (referred to as a target aptamer hereinafter) having a specific identification function on the target object and a nucleic acid fragment (referred to as capture probe DNA hereinafter) forming a partial base complementary sequence with the aptamer fragment, the aptamer fragment and the nucleic acid fragment are hybridized to form the probe body, wherein the 3' end of the nucleic acid fragment is thiolated; and the ability that the nucleic acid fragment competitively hybridizes with the aptamer fragment is weaker than the ability that the target object hybridizes with the aptamer fragment.

The second objective of the present invention is to provide an electrochemical biosensor including the biological probe used for detecting the target biomolecules, the electrochemical biosensor is prepared by the following steps:

under the initiation of the target object, through a competitive reaction, the nucleic acid aptamer fragment deviates from the biological probe that used for detecting the target biomolecules, and specifically binds with the target object;

adding an EXO I enzyme, wherein the EXO I enzyme hydrolyses the aptamer fragment present in a single chain form, at this time, the target object dissociates and continues to specifically bind with the aptamer fragment in the probe body so as to form a circular reaction in which hydrolysis is combined with specific binding and a target signal is amplified, and nano silver connected with the nucleic acid fragment (capture probe DNA) is obtained finally;

adding a complementary probe (referred to as a biological complementary probe hereinafter), wherein the complementary probe includes nano silver and a plurality of nucleic acid fragments (referred to as complementary probe DNA) that are connected to the surface of the nano silver and are in base complementary with the nucleic acid fragments, and the 3' ends of the nucleic acid fragments are thiolated; and gathering the nano silver subjected to the base complementation with the complementary probe on the surface of a gold electrode modified with the complementary probe DNA by using the base complementary pairing principle, wherein the obtained gold electrode is an electrochemical biosensor.

The nano silver is connected with the nucleic acid fragment (capture probe DNA) in the following situations: the first situation is that only the nucleic acid fragment (capture probe DNA) is connected to the nano silver, and the other situation is that not only the nucleic acid fragment (capture probe DNA) but also the probe body are connected to the nano silver.

The preparation method of the electrochemical biosensor based on the aptamer/nano silver probe and EXO I enzyme target cyclic amplification strategy in the present invention specifically includes the following steps:

(1) preparing the biological capture probe:

performing complementary pairing on the capture probe DNA with an opened disulfide bond with a target object aptamer to form probe body solution (double-chain DNA solution); performing a mixing reaction on the probe body solution and nano silver colloid to obtain the biological capture probe, wherein the 3' end of the capture probe DNA is thiolated;

(2) preparing the biological complementary probe:

performing a mixing reaction on the base complementary probe DNA of the capture probe DNA with the opened disulfide bond in the step (1) and the nano silver colloid to obtain the biological complementary probe, wherein the 3' end of the complementary probe DNA is thiolated;

(3) identifying the biological capture probe and amplifying an enzyme assisted target cyclic shearing signal:

performing the mixing reaction on the biological capture probe obtained in the step (1), the target object and EXOI exonuclease; and (4) preparing the electrochemical biosensor:

adding the solution obtained in the step (3) to the biological complementary probe obtained in the step (2), meanwhile soaking the gold electrode modified with the complementary probe DNA in the reaction solution to perform the mixing reaction, and taking out the electrode to obtain the electrochemical biosensor.

The sequence of the above steps can be adjusted according to actual situations.

In the step (1), the target object aptamer specifically binds with the target object, preferably, when the target object is lysozyme, the DNA sequence of the capture probe is: 5'-A CTC TTT AGC CCT GAT-C6-SH-3', and the sequence is as shown by SEQID NO: 1; and the sequence of the lysozyme aptamer is: 5'-ATC AGG GCT AAA GAG TGC AGA GTT ACT TAG-3', and the sequence is as shown by SEQID NO: 2.

When the target object is interferon γ (IFN-γ), the DNA sequence of the capture probe is: 5'-CC AAC ACA ACC AAC CCC-C6-SH-3', and the sequence is as shown by SEQID NO: 4; and the sequence of the γ interferon aptamer is: 5'-GGG GTT GGT TGT GTT GGG TGT TGT GTC CAA CCC C-3', and the sequence is as shown by SEQID NO: 5.

Preferably, the concentration of the capture probe DNA is 100 μM, and the concentration of the target object aptamer is 100 μM. The volume ratio of the capture probe DNA to the target object aptamer to the nano silver colloid is (0.5-1.5):(0.5-1.5):100.

The disulfide bond of the probe can be opened by using a thiol reducing agent and other methods, preferably, the preparation method of the capture probe DNA with the opened disulfide bond is as follows: reacting the capture probe DNA with a solution containing tris(2-carboxyethyl) phosphine to open the disulfide bond, wherein the concentration of the tris(2-carboxyethyl) phosphine in the solution containing the tris(2-carboxyethyl) phosphine is 0.01 M, the concentration of PB is 0.01M, the concentration of NaCl is 0.1M, and the reaction time is 0.5-1.5 h (preferably 1 h).

The specific reaction step of the probe body solution (double-chain DNA solution) is as follows: reacting at 35-40° C. for 1.5-2.5 h, preferably reacting at 37° C. for 2 h.

The conditions of the mixing reaction are as follows: providing a sealed and dark environment, stirring at 35-40° C. to react for 5-6 h, and reacting at 2-6° C. for 10-14 h.

In order to further stabilize the obtained biological capture probe, the following steps are executed: reacting at 2-6° C. for 10-14 h, adding a PBS buffer solution into the reactants under a stirring condition to adjust the pH, adding a NaCl solution, stirring for 2-4 h in the sealed and dark environment, reacting overnight (the reaction time is 10-24 h) at 2-6° C. in the sealed and dark environment, and performing PBS centrifugal washing to obtain the biological capture probe.

In the step (2), when the target is lysozyme, the sequence of the complementary probe DNA is: 5'-ATC AGG GCT AAA GAG T-C6-SH-3', and the sequence is as shown by SEQID NO: 3, when the target object is the r interferon, the sequence of the complementary probe DNA is: 5'-GGG GTT GGT TGT GTT GG-C6-SH-3', and the sequence is as shown by SEQID NO: 6, and its concentration is 100 μM. The volume ratio of the complementary probe DNA to the nano silver colloid is 0.5-1.5:100.

The disulfide bond of the probe can be opened by using the thiol reducing agent and other methods, preferably, the preparation method of the complementary probe DNA with the opened disulfide bond is as follows: reacting the complementary probe DNA with the solution containing tris(2-carboxyethyl) phosphine to open the disulfide bond, wherein the concentration of the tris(2-carboxyethyl) phosphine in the solution containing the tris(2-carboxyethyl) phosphine is 0.01 M, the concentration of PB is 0.01 M, the concentration of NaCl is 0.1 M, and the reaction time is 0.5-1.5 h (preferably 1 h).

The conditions of the mixing reaction are as follows: providing the sealed and dark environment, stirring at 35-40° C. to react for 5-6 h, and reacting at 2-6° C. for 10-14 h.

In order to further stabilize the obtained biological complementary probe, the following steps are executed: reacting at 2-6° C. for 10-14 h, adding the PBS buffer solution into the reactants under the stirring condition to adjust the pH, adding the NaCl solution, stirring for 2-4 h in the sealed and dark environment, reacting (the reaction time is 10-24 h) at 2-6° C. in the sealed and dark environment, and performing PBS centrifugal washing to obtain the biological complementary probe.

In the step (1) and the step (2), the preparation method of the nano silver is as follows: slowly dripping 0.002 M silver nitrate into 0.003 M sodium borohydride of which the volume is 2-2.5 times of that of silver nitrate at a dripping speed of 1 milliliter every time in ice water bath under a vigorous stirring condition, and continuously stirring for 5 min vigorously after all silver nitrate is dripped; transferring the obtained reactants into boiling water bath, heating for 3-5 min, immediately adding a set amount of 0.003M sodium borohydride solution, moving out the reactants from the hot water bath, and stirring vigorously the reactants to cool the same to the room temperature; and transferring the prepared nano silver colloid into a brown bottle soaked by aqua regia, and storing the nano silver colloid at 4° C. in darkness.

In the step (3), the target object is a to-be-measured object with set concentration or a to-be-measured object with unknown concentration, and the conditions of the mixing reaction are as follows: reacting at 35-40° C. for 0.5-1.5 h, and preferably, reacting at 37° C. for 1 h.

The volume ratio of the biological capture probe obtained in the step (1) to the target object is 1: 1-2, the adding amount of the EXOI exonuclease is 15-25 U, and preferably, the volume ratio of the biological capture probe obtained in the step (1) to the target object is 1:1, and the adding amount of the EXOI exonuclease is 20 U.

In the step (4), the volume ratio of the solution obtained in the step (3) to the biological complementary probe obtained in the step (2) is 1: 1-2, and preferably is 1:1.

The gold electrode requires a polishing treatment comprising the following treatment steps: grinding the gold electrode by using alumina powder, flushing the gold electrode with secondary water after grinding, and respectively performing ultrasonic cleaning and drying in ethanol and the secondary water to obtain the gold electrode subjected to the polishing treatment. Further, the polishing treatment comprises the following steps: sequentially grinding the gold electrode on chamois by using 0.3 μm and 0.05 μm alumina powder; firstly flushing the gold electrode with secondary water after grinding, then performing ultrasonic cleaning in the ethanol and the secondary water for 20-25 s, and air drying the gold electrode by using nitrogen.

The preparation method of the gold electrode modified with the complementary probe DNA includes the following steps: reacting the complementary probe DNA with TCEP for 2 h to open the disulfide bond, wherein in the reaction system for opening the disulfide bond of the complementary probe DNA, the concentration of DNA is 1 μM, the concentration of TCEP is 0.01 M, the concentration of PB is 0.01 M, and the concentration of NaCl is 0.1 M; and then soaking the complementary probe DNA with the opened disulfide bond in the polished gold electrode for 24 h to obtain the gold electrode modified with the complementary probe DNA.

The conditions of the mixing reaction are as follows: reacting at 35-40° C. for 1.5-2.5 h, and preferably, performing vibration reaction at 37° C. for 2 h.

The third objective of the present invention is to provide an application of the above electrochemical sensor for detecting the concentration of biomolecules, wherein the biomolecules include ATP, amino acids, nucleotide, toxin, enzymes, growth factors, cell adhesion molecules, viruses, bacteria and cells or other biomolecules capable of serving as aptamers. According to the inventive concept of the present invention, the concentration of various biomolecules can be detected, such as lysozyme, γ interferon, ATP or other biomolecules. The application method includes the following steps:

(1) performing electrochemical detection: performing LSV detection on the electrochemical biosensors of the target object of each standard concentration to obtain LSV peak current of the target object with a different standard concentration;

(2) drawing a standard curve: making a linear regression equation of logarithms of the concentration of the target object by using the LSV peak current in the step (1) to obtain the standard curve of the method; and (3) detecting an actual sample: performing electrochemical detection on the electrochemical sensor of the actual sample to obtain the corresponding LSV peak current, and substituting the LSV peak current into the standard curve in the step (2) to obtain the concentration of the target object in the actual sample.

In the step (1), the LSV detection conditions are as follows: the gold electrode is used as a working electrode, a calomel electrode is used as a reference electrode, and a platinum wire electrode is used as a contrast electrode to form a three-electrode system to perform the LSV detection.

An LSV detection solution is a PBS buffer solution, specifically: 0.2M PBS, and the preparation method is as follows: dissolving 1.78 g $Na_2HPO_4 \cdot 2H_2O$ in 1000 mL water to obtain a $Na_2HPO_4$ aqueous solution; dissolving 1.38 g $NaH_2PO_4 \cdot H_2O$ in 1000 mL water to obtain a $NaH_2PO_4$ aqueous solution; and uniformly mixing 810 mL $Na_2HPO_4$ aqueous solution, 190 mL $NaH_2PO_4$ aqueous solution and 11.69 g NaCl to obtain 0.2 M PBS with pH 7.4.

One of the above technical solutions has the following beneficial effects:

(1) the electrochemical biosensor based on the aptamer/nano silver biological probe and the EXO I enzyme target strategy in the present invention is a novel label-free electrochemical biosensor that uses nano silver particles having the functions of identifying the target object and generating electrochemical signals and modified by the aptamer as the biological probe for detecting the biomolecules, under the initiation of the target object and the assistance of the complementary probe and the EXO I enzyme cyclic shear amplification, and by means of the DNA complementary pairing principle, the probe can be gathered on the surface of the gold electrode, the larger the concentration of the target biomolecules is, the larger the gathering degree of the induced aptamer/nano silver probe is, and meanwhile the EXO I enzyme target cyclic amplification mechanism is introduced in the identification process of the target object, so that the electrochemical biosensor can sensitively and efficiently detect the target biological substances.

(2) Compared with other work, the present invention uses the aptamer/nano silver biological probe having two functions of identification and signal generation in the electrochemical biosensor for the first time, a signal substrate used by the traditional label-free detection method is omitted, so that the electrochemical biosensor is simple and convenient to operate, good in stability, low in detection limit, high in sensitivity and high in selectivity.

(3). Due to the electrochemical detection method, the present invention also has the advantages of being simple and convenient to operate, low in cost, fast and efficient, easy to miniaturize and the like, and being able to achieve onsite instant fast detection. Therefore, the electrochemical biosensor based on the aptamer/nano silver biological probe provides a sensitive and efficient novel method for detecting the biomolecules.

DETAILED DESCRIPTION OF THE EMBODIMENTS

The present invention will be further described with reference to the following embodiments.

Instruments and reagents used in the experiment are as follows: (1) the instruments: the CHI650 electrochemical workstation (Shanghai Chenhua Instrument Co., Ltd.); a saturated calomel electrode (SCE) used as a reference electrode and a platinum wire electrode used as a counter electrode; (2) the reagents: a lysozyme aptamer, a γ interferon aptamer and a reporting probe (Shanghai Bioengineering Co., Ltd.), the other reagents being analytically pure, and the experimental water being secondary distilled water.

Embodiment 1

Figure 1:
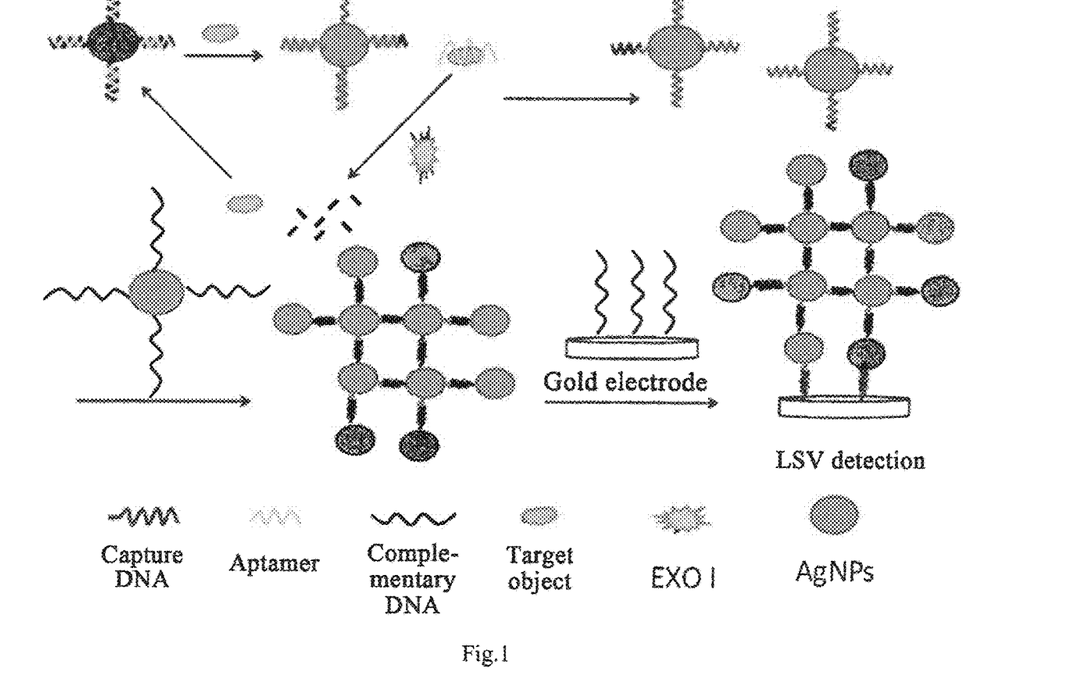
FIG. 1 is a schematic diagram of the present invention.

A preparation method of an electrochemical biosensor used for detecting lysozyme, as shown in FIG. 1, includes the following steps:

(1) Preparing nano silver: adding 100 ml 0.003M sodium borohydride in a 250 m three-necked round-bottom flask in ice water bath, sealing the left and right necks, and performing vigorous stirring; slowly adding 50 ml 0.002 M silver nitrate into sodium borohydride by using a pipette at a speed of 1 ml every time, waiting for 2 min once 10 ml silver nitrate is added, and continuing to perform vigorous stirring for 5 min after the silver nitrate is completely added; transferring the round-bottom flask in boiling water bath, heating for 3-5 min, and immediately and quickly adding 10 ml 0.003 M sodium borohydride solution; removing the flask from the hot water bath, and continuing to perform vigorous stirring to cool the flask to the room temperature; and transferring the prepared nano silver colloid into a brown bottle soaked by aqua regia, and storing the nano silver colloid at 4° C. in darkness.

(2) Preparing a capture probe: taking 10 μL capture probe DNA (5'-A CTC TTT AGC CCT GAT-C6-SH-3', and the sequence of which is as shown by SEQ ID NO: 1), adding 2 μL 0.01 M TCEP (0.01 M PB, 0.1 M NaCl) solution in the capture probe DNA in a 2 mL centrifugal tube, and standing for 1 h to open a disulfide bond; adding 10 μL lysozyme aptamer (5'-ATC AGG GCT AAA GAG TGC AGA GTT ACT TAG-3', and the sequence of which is as shown by SEQ ID NO: 2), and reacting at 37° C. for 2 h in a water bath kettle to form double chains; taking a 3 ml glass reaction flask, adding 1 ml nano silver colloid, adding double-chain DNA in the flask, slowly stirring for 5-6 h in a sealed and dark environment, taking out magnetons, and reacting at 4° C. for 12 h; 12 h later, adding 1221 μL 0.1M PBS buffer solution into the reaction flask to adjust the pH, and slowly stirring; and adding 21 μL 2M NaCl solution at a speed of 1 μL every time, slowly stirring for 3 h in the sealed and dark environment, standing overnight at 4° C. in the sealed and dark environment, and performing centrifugal washing by using 0.1M PBS.

(3) Preparing a complementary probe: taking 10 μL capture probe DNA (5'-ATC AGG GCT AAA GAG T-C6-SH-3', and the sequence of which is as shown by SEQ ID NO: 3), adding 2 μL 0.01 M TCEP (0.01 M PB, 0.1 M NaCl) solution in the capture probe DNA in the 2 mL centrifugal tube, and standing for 1 h to open the disulfide bond; taking a 3 ml glass reaction flask, adding 1 ml nano silver colloid, adding 10 μL complementary probe DNA for opening the disulfide bond in the flask, slowly stirring for 5-6 h in the sealed and dark environment, taking out the magneton, and reacting at 4° C. for 12 h; 12 h later, adding 122 μL 0.1M PBS buffer solution into the reaction flask to adjust the pH, and slowly stirring; and adding 21 μL 2M NaCl solution at a speed of 1 μL every time, slowly stirring for 3 h in the sealed and dark environment, standing overnight at 4° C. in the sealed and dark environment, and performing centrifugal washing by using 0.1M PBS.

(4) Configuring a lysozyme solution with standard concentration: configuring 100 uM mother solution by using ultrapure water, and configuring lysozyme solutions with concentration grades of 0.01 nM, 0.1 nM, 1 nM, 5 nM, 10 nM, 50 nM and 100 nM by using 0.1M PBS buffer solution to dilute the mother solution.

(5) Identifying the capture probe and amplifying an enzyme assisted target cyclic shear signal: adding 100 μL capture probe and 100 uL lysozyme with the gradient concentration in a 2 mL centrifugal tube, adding 20 U EXO I exonuclease, and reacting in a water bath kettle at 37° C. for 1 h.

(6) Preparing a gold electrode modified with the complementary probe DNA.

Polishing treatment of the gold electrode: sequentially grinding the gold electrode into a mirror surface on chamois by using 0.3 μm and 0.05 μm $Al_2O_3$, and sequentially performing ultrasonic cleaning for 20-25 s by using ethanol and secondary water; and then performing cyclic voltammetry in 0.5M sulfuric acid solution, sweeping the gold electrode at a speed of 0.1 V/s until the gold electrode is stable, flushing the gold electrode with the secondary water, and air drying the gold electrode by using nitrogen; and reacting the complementary probe DNA with TCEP for 2 h to open the disulfide bond, wherein in the reaction system for opening the disulfide bond of the complementary probe DNA, the concentration of DNA is 1 μM, the concentration of TCEP is 0.01 M, the concentration of PB is 0.01 M, and the concentration of NaCl is 0.1 M; and then soaking the complementary probe DNA with the opened disulfide bond in the polished gold electrode for 24 h to obtain the gold electrode modified with the complementary probe DNA.

(7) Preparing an Electrochemical Biosensor

Respectively adding the solutions obtained in the step (5) to the biological complementary probe obtained in the step (3), then soaking the gold electrode modified with the complementary probe DNA in the reaction solution to perform a mixing reaction, and taking out the electrode to obtain the electrochemical biosensor under each concentration gradient.

Embodiment 2

(1) Preparing a capture probe: taking 10 μL capture probe DNA (5'-A CTC TIT AGC CCT GAT-C6-SH-3', and the sequence of which is as shown by SEQ ID NO: 1), adding 2 μL 0.01 M TCEP (0.01 M PB, 0.1 M NaCl) solution in the capture probe DNA in a 2 mL centrifugal tube, and standing for 1 h to open a disulfide bond; adding 10 L lysozyme aptamer (5'-ATC AGG GCT AAA GAG TGC AGA GTT ACT TAG-3', and the sequence of which is as shown by SEQ ID NO: 2), and reacting at 37° C. for 1.5 h in a water bath kettle to form double chains; taking a 3 ml glass reaction flask, adding 1 ml nano silver colloid, adding double-chain DNA in the flask, slowly stirring for 5-6 h in a sealed and dark environment, taking out magnetons, and reacting at 5° C. for 13 h; 13 h later, adding 122 μL 0.1M PBS buffer solution into the reaction flask to adjust the pH, and slowly stirring; and adding 21 μL 2M NaCl solution at a speed of 1 μL every time, slowly stirring for 3 h in the sealed and dark environment, standing overnight at 4° C. in the sealed and dark environment, and performing centrifugal washing by using 0.1M PBS.

(2) Preparing a complementary probe: taking 10 μL complementary probe DNA (5'-ATC AGG GCT AAA GAG T-C6-SH-3', and the sequence of which is as shown by SEQ ID NO: 3), adding 21 L 0.01 M TCEP (0.01 M PB, 0.1 M NaCl) solution in the capture probe DNA in the 2 mL centrifugal tube, and standing for 1 h to open the disulfide bond; taking a 3 ml glass reaction flask, adding 1 ml nano silver colloid, adding 10 μL complementary probe DNA for opening the disulfide bond in the flask, slowly stirring for 5-6 h in the sealed and dark environment, taking out the magnetons, and reacting at 5° C. for 13 h; 13 h later, adding 122 μL 0.1M PBS buffer solution into the reaction flask to adjust the pH, and slowly stirring; and adding 21 μL 2M NaCl solution at a speed of 1 μL every time, slowly stirring for 3 h in the sealed and dark environment, standing overnight at 4° C. in the sealed and dark environment, and performing centrifugal washing by using 0.1M PBS.

(3) Configuring a lysozyme solution with standard concentration: configuring 100 uM mother solution by using ultrapure water, and configuring lysozyme solutions with concentration grades of 0.01 nM, 0.1 nM, 1 nM, 5 nM, 10 nM, 50 nM and 100 nM by using 0.1M PBS buffer solution to dilute the mother solution.

(4) Identifying the capture probe and amplifying an enzyme assisted target cyclic shear signal: adding 100 μL capture probe and 100 uL lysozyme with the gradient concentration in a 2 mL centrifugal tube, adding 20 U EXO I exonuclease, and reacting in a water bath kettle at 35° C. for 1.5 h.

(5) Preparing an electrochemical biosensor

Respectively adding the solutions obtained in the step (4) to the biological complementary probe obtained in the step (2), then soaking the gold electrode modified with the complementary probe DNA in the step (6) in embodiment 1 in the reaction solution to perform a mixing reaction, and taking out the modified electrode to obtain the electrochemical biosensor under each concentration gradient.

Embodiment 3

An application method of measuring lysozyme concentration by using the electrochemical biosensor prepared in embodiment 1 includes the following steps:

(1) Performing electrochemical detection: taking out the electrodes obtained in embodiment 1, flushing the electrodes with 0.01M PB for 2-3 times, soaking the electrodes in 0.2M PBS detection liquid to perform LSV detection with a three-electrode system consisting of a calomel reference electrode and a platinum wire contrast electrode.

Figure 2:
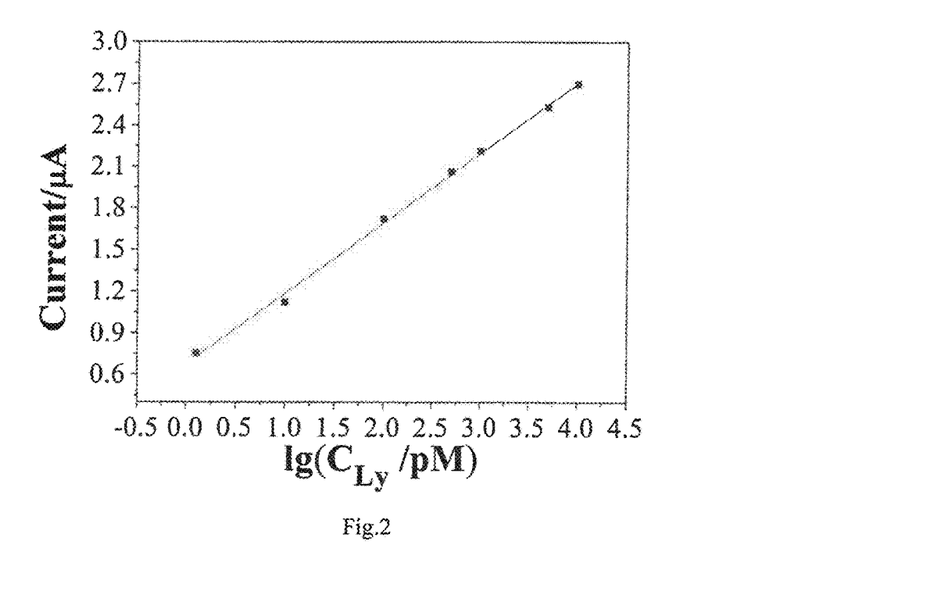
FIG. 2 is a linear relation diagram of detecting lysozyme in the present invention.

(2) Drawing a standard curve: making a linear regression equation of logarithms of the lysozyme concentration by using the LSV peak current after the lysozyme with the standard concentration is identified to obtain the standard curve of the method, as shown in FIG. 2, the linear regression equation is I=0.50681 gC+0.67798, $R^2$=0.997, the linear range is 1.5 pM-10 nM, and the detection limit is 290 fM(S/N=3).

(3) Detecting an actual sample: performing operations on the actual sample according to the method in embodiment 1, and substituting the obtained peak current into the standard curve to obtain the concentration of the lysozyme in the actual sample.

A lysozyme detection result shows that the peak current curves of lysozyme with different concentrations change obviously, the lysozyme had a good linear relationship with the concentration of 1.5 pM-10 nM, and the detection limit of the electrochemical biosensor of the present invention on the lysozyme can be as low as 290 fM.

Embodiment 4

A preparation method of an electrochemical biosensor for detecting γ interferon includes the following steps:

(1) Preparing nano sliver: the same as the preparation steps of the nano sliver in embodiment 1.

(2) Preparing a capture probe: taking 10 μL capture probe DNA (5'-CC AAC ACA ACC AAC CCC-C6-SH-3', and the sequence of which is as shown by SEQ ID NO: 4), adding 2 μL 0.01 M TCEP (0.01 M PB, 0.1 M NaCl) solution in the capture probe DNA in a 2 mL centrifugal tube, and standing for 1 h to open a disulfide bond; adding 10 μLγ interferon aptamer (5'-GGG GTT GGT TGT GTT GGG TGT TGT GTC CAA CCC C-3', and the sequence of which is as shown by SEQ ID NO: 5), and reacting at 37° C. for 2 h in a water bath kettle to form double chains; taking a 3 ml glass reaction flask, adding 1 ml nano silver colloid, adding double-chain DNA in the flask, slowly stirring for 5-6 h in a sealed and dark environment, taking out magnetons, and reacting at 4° C. for 12 h; 12 h later, adding 122 μL 0.1M PBS buffer solution into the reaction flask to adjust the pH, and slowly stirring; and adding 21 μL 2M NaCl solution at a speed of 1 μL every time, slowly stirring for 3 h in the sealed and dark environment, standing overnight at 4° C. in the sealed and dark environment, and performing centrifugal washing by using 0.1M PBS.

(3) Preparing a complementary probe: taking 10 μL complementary probe DNA (5'-GGG GTT GGT TGT GTT GG-C6-SH-3', and the sequence of which is as shown by SEQ ID NO: 6), adding 2 μL 0.01 M TCEP (0.01 M PB, 0.1 M NaCl) solution in the capture probe DNA in the 2 mL centrifugal tube, and standing for 1 h to open the disulfide bond; taking a 3 ml glass reaction flask, adding 1 ml nano silver colloid, adding 10 μL complementary probe DNA for opening the disulfide bond in the flask, slowly stirring for 5-6 h in the sealed and dark environment, taking out the magnetons, and reacting at 4° C. for 12 h; 12 h later, adding 122 μL 0.1M PBS buffer solution into the reaction flask to adjust the pH, and slowly stirring; and adding 21 μL 2M NaCl solution at a speed of 1 μL every time, slowly stirring for 3 h in the sealed and dark environment, standing overnight at 4° C. in the sealed and dark environment, and performing centrifugal washing by using 0.1 M PBS.

(4) Configuring a γ interferon solution with standard concentration: configuring 100 uM mother solution by using ultrapure water, and configuring γ interferon solutions with concentration grades of 0.01 nM, 0.1 nM, 1 nM, 5 nM, 10 nM, 50 nM and 100 nM by using 0.1M PBS buffer solution to dilute the mother solution.

(5) Identifying the capture probe and amplifying an enzyme assisted target cyclic shear signal: adding 100 μL capture probe and 100 uL γ interferon with the gradient concentration in 2 mL centrifugal tube, adding 20 U EXO I exonuclease, and reacting in a water bath kettle at 37° C. for 1 h.

(6) Preparing a gold electrode modified with the complementary probe DNA.

Polishing treatment of the gold electrode: sequentially grinding the gold electrode into a mirror surface on chamois by using 0.3 μm and 0.05 μm $Al_2O_3$, and sequentially performing ultrasonic cleaning for 20-25 s by using ethanol and secondary water, and then performing cyclic voltammetry in 0.5M sulfuric acid solution, sweeping the gold electrode at a speed of 0.1 V/s until the gold electrode is stable, flushing the gold electrode with the secondary water, and air drying the gold electrode by using nitrogen;

reacting the complementary probe DNA with TCEP for 2 h to open the disulfide bond, wherein in the reaction system for opening the disulfide bond of the complementary probe DNA, the concentration of DNA is 1 μM, the concentration of TCEP is 0.01 M, the concentration of PB is 0.01 M, and the concentration of NaCl is 0.1 M; and then soaking the complementary probe DNA with the opened disulfide bond in the polished gold electrode for 24 h to obtain the gold electrode modified with the complementary probe DNA.

(7) Preparing an electrochemical biosensor

Respectively adding the solutions obtained in the step (5) to the biological complementary probe obtained in the step (3), then soaking the gold electrode modified with the complementary probe DNA in the reaction solution to perform a mixing reaction, and taking out the electrode to obtain the electrochemical biosensor under each concentration gradient.

LSV detection is performed on the electrochemical biosensor in embodiment 4, the electrochemical biosensor prepared in embodiment 4 of the present invention can detect the concentration of the γ interferon, the peak current curves of γ interferon with different concentrations change obviously, and the detection limit of the electrochemical biosensor of the present invention on the γ interferon can be as low as an fM level.

The above embodiments are preferred embodiments of the present invention. However, the embodiments of the present invention are not limited to the above embodiments. Any other changes, modifications, substitutions, combinations and simplifications made without departing from the spirit essence and principle of the present invention shall be equivalent substitutions, and are all incorporated in the protection scope of the present invention.

The invention claimed is:

1. A biological probe having the functions of identifying a target object and generating electrochemical signals and being used for detecting target biomolecules, the biological probe comprising:
   a first silver nanoparticle; and
   a plurality of probe bodies connected to the surface of the first silver nanoparticle, each probe body comprising:
      an aptamer fragment that specifically binds to the target object, and
      a first nucleic acid fragment hybridized to the aptamer fragment, the first nucleic acid fragment forming a partial base complementary sequence with the aptamer fragment and having a thiolated 3' end,
   wherein the ability of the first nucleic acid fragment to competitively hybridize with the aptamer fragment is weaker than the ability of the target object to hybridize with the aptamer fragment.

2. A method for preparing the biological probe of claim 1, the method comprising:
   performing complementary pairing on the first nucleic acid fragment with an opened disulfide bond and the aptamer fragment to form a probe body solution comprising the probe bodies; and
   performing a mixing reaction on the probe body solution and a first nano silver colloid comprising the first silver nanoparticles to obtain the biological probe used for detecting the target biomolecules.

3. The method of claim 2, wherein:
   the first nucleic acid fragment with the opened disulfide bond is prepared by reacting the first nucleic acid fragment with a solution containing tris(2-carboxyethyl) phosphine to open the disulfide bond;
   the complementary pairing is performed at 35-40° C. for 1.5-2.5 h;
   the mixing reaction comprises providing a sealed and dark environment, stirring the probe body solution and the first nano silver colloid at 35-40° C. to react for 5-6 h, and reacting at 2-6° C. for 10-14 h; and
   the method further comprises, after reacting at 2-6° C. for 10-14 h, adding a PBS buffer solution into the reactants under a stirring condition to adjust the pH, adding a NaCl solution, stirring for 2-4 h in the sealed and dark environment, reacting at 2-6° C. for 10-24 h in the sealed and dark environment, and performing PBS centrifugal washing to obtain the biological probe used for detecting the target biomolecules.

4. An electrochemical biosensor comprising the biological probe of claim 1, the electrochemical biosensor prepared by the following steps:
   under the initiation of the target object, through a competitive reaction, causing the nucleic acid aptamer fragment to deviate from the biological probe used for detecting the target biomolecules, and to specifically bind with the target object;
   adding an EXO I enzyme, which hydrolyses the aptamer fragment present in a single chain form so that the target object dissociates from and continues to specifically bind with the aptamer fragment in the probe body in a circular reaction in which hydrolysis is combined with specific binding and a target signal is amplified, and a solution containing the first silver nanoparticle connected with the first nucleic acid fragment is obtained finally;
   adding a complementary probe to the solution, the complementary probe comprising:
      a second silver nanoparticle; and
      a plurality of second nucleic acid fragments that are connected to the surface of the second silver nanoparticle and are base complementary with the first nucleic acid fragment, wherein the 3' ends of the second nucleic acid fragments are thiolated; and
   gathering the first silver nanoparticle subjected to the base complementation with the complementary probe on the surface of a gold electrode modified with the second nucleic acid fragment by using the base complementary pairing principle, wherein the obtained gold electrode is an electrochemical biosensor.

5. The electrochemical biosensor of claim 4, wherein:
   the complementary probe is prepared by a method comprising performing a mixing reaction on (i) the second nucleic acid fragment with an opened disulfide bond and (ii) a second nano silver colloid comprising the second silver nanoparticles to obtain the complementary probe;
   the second nucleic acid fragment with the opened disulfide bond is prepared by reacting the second nucleic acid fragment with a solution containing tris(2-carboxyethyl) phosphine to open the disulfide bond so as to obtain the second nucleic acid fragment with the opened disulfide bond;
   the mixing reaction comprises providing a sealed and dark environment, stirring at 35-40° C. to react for 5-6 h, and reacting at 2-6° C. for 10-14 h; and
   the method for preparing the complementary probe further comprises, after reacting at 2-6° C. for 10-14 h, adding a PBS buffer solution into the reactants under a stirring condition to adjust the pH, adding a NaCl solution, stirring for 2-4 h in the sealed and dark environment, and reacting at 2-6° C. for 10-24 h in the sealed and dark environment, and performing PBS centrifugal washing to obtain the complementary probe.

6. The electrochemical sensor of claim 4, wherein the target object is selected from the group consisting of ATP, amino acids, nucleotide, toxin, enzymes, growth factors, cell adhesion molecules, viruses, bacteria, cells, and other biomolecules capable of serving as aptamers.

7. The biological probe according to claim 1, wherein:
   the target object is a lysozyme,
   the nucleic acid fragment comprises the nucleic acid sequence of SEQ ID NO: 1, and
   the aptamer fragment comprises the nucleic acid sequence of SEQ ID NO: 2.

8. The biological probe according to claim 1, wherein:
   the target object is interferon γ,
   the nucleic acid fragment comprises the nucleic acid sequence of SEQ ID NO: 4, and
   the aptamer fragment comprises the nucleic acid sequence of SEQ ID NO: 5.

9. A method of detecting the concentration of a target object in an actual sample, the method comprising:
   (1) performing electrochemical detection: performing LSV detection on each of a plurality of electrochemical biosensors according to claim 4 that were prepared using varying concentrations of the target object in order to obtain an LSV peak current of the target object at each of the concentrations;

(2) drawing a standard curve: making a linear regression equation of logarithms of the concentration of the target object by using the LSV peak current to obtain a standard curve; and (3) detecting a concentration in an actual sample: performing electrochemical detection on an electrochemical sensor according to claim 4 prepared from the actual sample to obtain the corresponding LSV peak current, and substituting the LSV peak current into the standard curve to obtain the concentration of the target object in the actual sample.

10. The method of claim 9, wherein the target object is selected from the group consisting of ATP, amino acids, nucleotide, toxin, enzymes, growth factors, cell adhesion molecules, viruses, bacteria, cells, and other biomolecules capable of serving as aptamers.

11. The method of claim 9, wherein the LSV detection is performed using a three-electrode system comprising:
the electrochemical sensor as a working electrode,
a calomel electrode as a reference electrode, and
a platinum wire electrode as a contrast electrode.

12. The application of claim 11, wherein the LSV detection solution is a PBS buffer solution.

\* \* \* \* \*